United States Patent [19]
Yamazaki et al.

[11] Patent Number: 5,061,263
[45] Date of Patent: Oct. 29, 1991

[54] LIQUID COLLECTION TUBE

[75] Inventors: Sakae Yamazaki; Takato Murashita, both of Yamanashi, Japan

[73] Assignee: Terumo Kabushiki Kaisha, Tokyo, Japan

[21] Appl. No.: 478,673

[22] Filed: Feb. 12, 1990

[30] Foreign Application Priority Data

Feb. 13, 1989 [JP] Japan .................................. 1-34474
Feb. 15, 1989 [JP] Japan .................................. 1-37050

[51] Int. Cl.⁵ ............................................ A61B 19/00
[52] U.S. Cl. .................................. 604/403; 604/415; 215/247
[58] Field of Search ................ 604/403, 415; 215/247, 215/248, DIG. 3; 128/760

[56] References Cited

U.S. PATENT DOCUMENTS

| | | | |
|---|---|---|---|
| 1,189,465 | 7/1916 | Mayo | 604/415 |
| 2,338,108 | 1/1944 | Fields | 604/415 |
| 3,552,591 | 1/1971 | Wimmer | 215/DIG. 3 |
| 3,823,840 | 7/1974 | Zackheim | 215/247 |
| 4,301,936 | 11/1981 | Percarpio | 215/247 |
| 4,362,250 | 12/1982 | Cottingham | 215/247 |
| 4,772,558 | 9/1988 | Hammann | 215/247 |

*Primary Examiner*—Stephen C. Pellegrino
*Assistant Examiner*—Michael Rafa
*Attorney, Agent, or Firm*—Frishauf, Holtz, Goodman & Woodward

[57] ABSTRACT

A liquid collection tube for collecting blood or like liquid with a liquid collection needle, comprises a tube member with a bottom and a cap member removably fitted on an open end of the tube, with thread structures. A sealing member is interposed between the cap member and open end of the tube member to enhance the close contact between the two. The sealing member is not bonded to the open end of the tube member, and it can be removed together with the cap member to open the open end of the tube member when the cap member is removed from the tube member. The cap member has a through hole permitting a re-sealing member of the sealing member to be pierced from the outside.

23 Claims, 2 Drawing Sheets

FIG.1
FIG.2
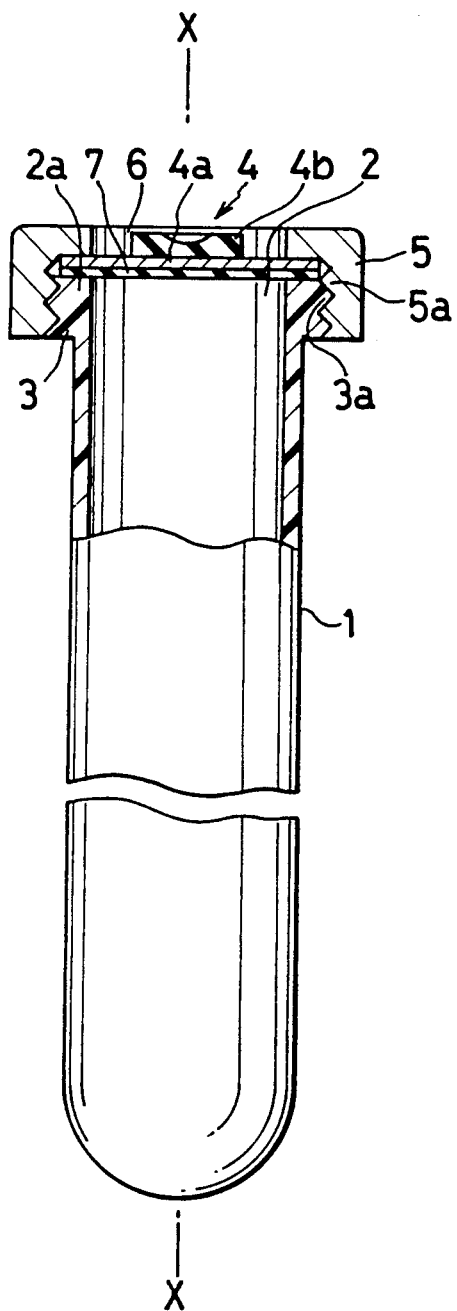
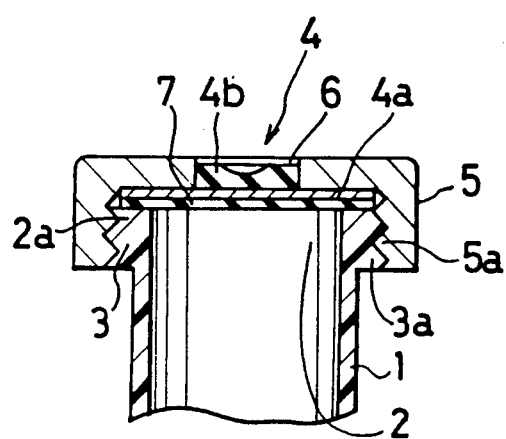

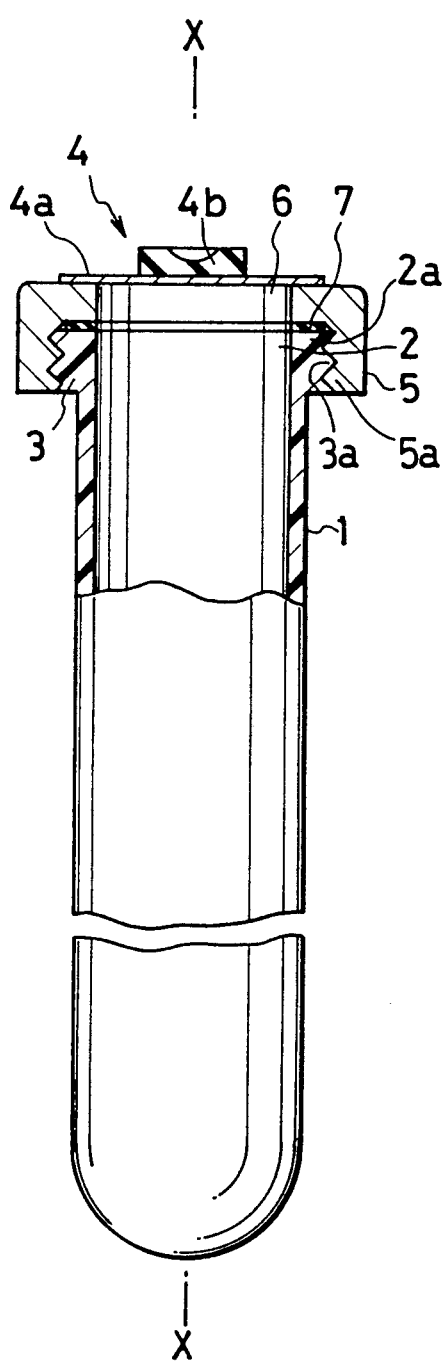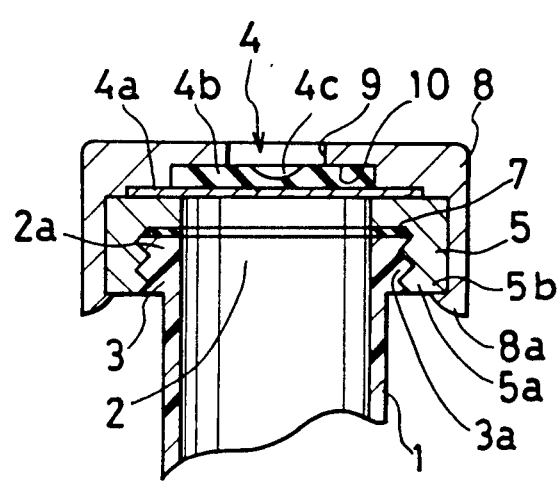

LIQUID COLLECTION TUBE

BACKGROUND OF THE INVENTION

This invention relates to a liquid collection tube for collecting blood or like liquid in it with a liquid collection needle and, more particularly, a liquid collection tube of a commonly termed film seal type, which is provided with a film member having a gas barrier character and a re-sealing member as sealing members.

A prior art liquid collection tube, for instance a blood collection tube used for blood examination, has a glass or plastic tube member with a bottom and a sealing member sealing an open end of the tube member. The sealing member consists of a film-like gas barrier member made from an aluminum foil, for instance, and a re-sealing member secured to the gas barrier film member and capable of re-sealing a pierced portion of the film member after removal of the needle.

In the blood collection tube of this film seal type, the gas barrier film member is bonded by an adhesive to a flange of the tube member adjacent to the open end thereof, and the re-sealing member is bonded to the gas barrier film member.

With this prior art blood collection tube, the gas barrier film member and re-sealing member are bonded by using an adhesive. Therefore, the bonding operation is cumbersome. In addition, once these members are bonded, they can not be readily peeled off. Further, in case of taking out a portion of collected blood for the purpose of analysis by piercing the sealing member and subsequently re-sealing the piercing member, the pierced sealing member can not be used again, and therefore it is necessary to prepare a new sealing member.

SUMMARY OF THE INVENTION

The present invention has been developed in view of the above, and its object is to provide a liquid collection tube, which does not require any cumbersome bonding operation, can be assembled easily, can be readily opened and closed and permits re-use of the sealing member.

To attain the above object of the invention, there is provided a liquid collection tube for collecting a liquid in its inside with a liquid collection needle, comprising a cylindrical tube member with a bottom, having an open end and closed at the other end, a cap member removably mounted on said tube member at said open end thereof and having a needle insertion through hole corresponding in position to said open end of said tube member, sealing means disposed in correspondence to said tube member and including a gas barrier film element for holding said open end of said tube member hermetically sealed, and a sealing member interposed between said cap member and said open end of said tube member and enhancing the close contact of said cap member with said open end of said tube member.

In this liquid collection tube, said gas barrier film element of said sealing means is disposed in an overlapped relation to said sealing member, and said cap member urges an edge portion of said sealing member and gas barrier film element overlapped over each other against the end surface of said open end of said tube member.

Further, as a preferred arrangement, said sealing means further includes a re-sealing element secured to said gas barrier film element, said re-sealing element being located in a through hole of said cap member.

As a further preferred arrangement, said tube member has a first thread formed on the outer periphery of said open end, and said cap member has a second thread formed on its inner periphery and meshed with said first thread.

With the above arrangement of said liquid collection tube according to the invention, with the cap member fitted on the open end of the tube member with a bottom, the sealing means is urged against the open end of the tube member and secured to the same with the sealing member interposed between the gas barrier film element and the open end of the tube member. Thus, the open end is sealed without use of any adhesive. This means that when the cap member is removed, the sealing means can also be removed. Since the sealing member is interposed between the gas barrier film element and the open end of the tube member, satisfactory close contact between the two can be obtained. Further, with an arrangement in which the cap member is screwedly fitted on the tube member with a bottom, the liquid collection tube can be readily assembled, and the open end can be readily opened and closed.

Thus, with the liquid collection tube according to the invention the open end of the tube member with a bottom can be readily sealed without need of any cumbersome bonding operation. Thus, the liquid collection tube can be readily assembled, and the open end can be readily opened and closed, and further the gas barrier film element and re-sealing element constituting the sealing means can be reused, thus simplifying the handling.

As a still further preferred arrangement of the liquid collection tube according to the invention, said sealing means is provided on said cap member to close the through hole of said cap member, thereby permitting said sealing means to be removed together with said cap member from said tube member.

As a further preferred arrangement, said sealing means includes a re-sealing element secured to said gas barrier film element on the side thereof opposite said open end of said tube member.

As a yet further preferred arrangement of the liquid collection tube according to the invention, said gas barrier film element of said sealing means is disposed on the outer end surface of said cap member such that the peripheral wall of said gas barrier film element is in contact with the outer end surface of said cap member and that the through hole of said cap is closed, and the liquid collection tube further comprises a second cap member for urging the outer periphery of said film element against the outer end surface of said first-mentioned cap member, said second cap member having a needle insertion through hole communicating with said through hole of said first-mentioned cap member via sealing means and a hook engaging with said first-mentioned cap member to permit said first and second cap members to be removed together with said sealing means from said tube member.

As a further preferred arrangement, said sealing member further includes a re-sealing member overlapped over said gas barrier film element, said second cap member has a recess for accommodating said re-sealing element when said second cap member is fitted on said first cap member, and said recess of said second cap member has a wall surface urging said re-sealing element together with said gas barrier film element against said first cap member.

With the above arrangement of the liquid collection tube according to the invention, the open end of the tube member is sealed by fitting the first cap member on the open end of the tube member with the sealing member interposed between the two and securing the sealing means to the first cap member. In case of removing the first cap member for distributing or collecting the collected liquid, the sealing means, which is secured to the cap member, is also removed, and thus it is possible to re-use the sealing means. Further, with an arrangement where the cap member is screwedly fitted on the tube member, the operation of assembling the liquid collection tube and operation of opening and closing the open end of the tube member can be further simplified.

Thus, with the liquid collection tube according to the invention the sealing operation, i.e., assembling operation, is simplified, the operation of removing the sealing means from the open end of the tube member is also simplified, and the sealing means can be re-used. Further, with an arrangement where the sealing means is urged against and secured to the first cap member by fitting the second cap member thereon, the sealing means can be accommodated inside, thus reducing the possibility of contact of blood with a person.

BRIEF DESCRIPTION OF THE DRAWINGS

FIG. 1 is a side view, partly broken apart, showing a reduced pressure blood collecting tube as a first embodiment of the invention;

FIG. 2 is a fragmentary sectional view showing a second embodiment obtained by modifying the first embodiment of the reduced pressure blood tube shown in FIG. 1;

FIG. 3 is a side view, partly broken apart, showing a reduced pressure blood tube as a third embodiment of the invention; and FIG. 4 is a fragmentary sectional view showing a fourth embodiment obtained by modifying the third embodiment of the reduced pressure blood collection tube according to the invention.

DESCRIPTION OF THE PREFERRED EMBODIMENTS

FIG. 1 is a side view, partly broken away, showing a reduced pressure blood collection tube as a first embodiment of the invention. Referring to the Figure, reference numeral 1 designates a cylindrical tube member with a bottom. Tube member 1 is made of a plastic material, for instance polyethylene telephthalate (PET) and has top opening 2 having a predetermined inner diameter. It has integral flange 3 provided on the outer periphery of its open end 2a in its axial direction X—X. Open end 2 of tube member 1 is sealed by sealing member 4 as sealing means with an anticoagulation agent or the like sealed in the tube member and with a predetermined reduced pressure maintained in the tube member. Sealing member 4 has gas barrier film member 4a, which closes open end 2 with its edge positioned on flange 3 of tube member 1, and re-sealing member 4b, which is made of natural rubber, for instance, and is secured to gas barrier film member 4a. The "gas barrier" does not mean only those materials which perfectly block gas (such as oxygen gas, carbon dioxide gas and water steam) but also means those permeable to gas to an extent of $0.1 \times 10^{-10}$ ml mm/cm$^2$ sec cmHg (20° C.) in case of oxygen gas and $1 \times 10^{-3}$ g mm/m$^2$ 24 h. (40° C., 90% RH) in case of steam. Generally, it means a material that has practical "gas barrier character". Re-sealing member 4b serves to re-seal a locality pierced by a needle (not shown) after blood collection as will be described later. The back side of gas barrier film member 4a is lined with thin sealing member (lining rubber) with a thickness of 0.1 mm, for instance, with respect to open end 2 of tube member 1. Sealing member 7 improves the close contactness between gas barrier film member 4a and open end 2 of tube member 1.

Both sealing member 7 and gas barrier film member 4a are held urged against open end 2a of tube member 1 by cap member 5. Cap member 5 is made of aluminum foil or like metal foil. It has needle insertion hole 6 formed at its center including axis X—X, and its inner peripheral wall is formed with female thread 5a as a second thread. In correspondence to female thread 5a the outer periphery of flange 3 of tube member 1 is formed with male thread 3a as a first thread.

When mounting cap member 5 on tube member 1, it is screwed by turning its head. In this way, sealing member 7 and gas barrier film member 4a can be readily and firmly urged against open end 2a of tube member 1. Re-sealing member 4b is secured by adhesive to gas barrier film member 4a in an overlapped relation thereto prior or subsequent to the fitting of cap member 5 on tube member 1. In a vacuum, cap member 5 can be difficultly fitted on tube member 1. Therefore, cap member 5 is first loosely fitted, and then in vacuum it is tightened. By so doing, the extent of turning of cap member 5 in a vacuum can be reduced, and the operation thus can be correspondingly facilitated.

When collecting blood, a hollow needle which is provided in a needle holder (not shown) is inserted through needle insertion through hole 6 of cap member 5, and forced to pierce re-sealing member 4b, gas barrier film member 4a and sealing member 7 into tube member 1. Blood introduced from the tip of the needle flows through the hollow needle into the tube member 1 due to a reduced pressure state in tube member 1, and blood collection is performed in this way. When separating components of collected blood, cap member 5 is removed from tube member 1 by loosening it, whereby gas barrier film member 4a and re-sealing member 4b can be readily removed together with sealing member 7. These components may be used again when sealing the tube again.

Preferably, gas barrier film member 4a and cap member may be bonded together in advance by coating an adhesive on a portion of the gas barrier film member 4a in contact with cap member 5. In this case, when cap member 5 is removed, gas barrier film member 4a and sealing member 7 may be removed simultaneously. Further, by coating an adhesive over the entire upper surface of gas barrier film member 4a the operation of securing re-sealing member 4b to member 4a may be facilitated.

FIG. 2 shows a second embodiment as a modification of the first embodiment described above, with parts like those in FIG. 1 designated by like reference numerals and symbols. In this embodiment, the inner diameter of needle insertion through hole 6 of cap member 5 is reduced to be substantially equal to the outer diameter of re-sealing member 4b, and re-sealing member 4b is fitted in needle insertion hole 6, as shown in FIG. 2, Thus, occasional detachment of cap member 5 can be highly reliably prevented. Besides, the integrality of sealing means 4 and cap member 5 with each other and the sealing effect are also increased.

In the above first and second embodiments, cap member 5 is screwedly fitted on tube member 1 with a bottom, so that occasional detachment of cap member 5 can be highly reliably prevented. However, this construction is by no means limitative; for instance a cap member without any thread may be fitted with strong friction on the outer periphery of open end 2 of tube member 1. Further, in this case, the inner periphery of the lower end of the cap member may be provided with an annular engaging portion capable of elastic deformation to engage with the lower end of flange 3 of tube member 1. In this case, the cap member may be more firmly fitted on the tube member such that it will not be occasionally detached.

Further, while in the above first and second embodiments sealing member 7 is in the form of a disk overlapped over gas barrier film member 4a, it is also possible to use a ring-like sealing member having an opening corresponding to the open end of tube member 1, Further, by using a sealing member having an increased thickness, it is possible to let the sealing member also serve the role of re-sealing member 4b, thus dispensing with re-sealing member 4b and simplifying the structure.

FIG. 3 shows a third embodiment of the invention, with parts like those in the first embodiment of FIG. 1 designated by like reference numerals and symbols.

The third embodiment of according to the invention, show in a sectional view of FIG. 3, is a reduced pressure blood collection tube. Referring to the Figure, reference numeral 1 designates a cylindrical tube member with a bottom. Tube member 1 is made of a plastic material, for instance polyethylene telephthalate (PET), and it has top open end in it s axial direction X—X. It has flange 3 provided on the outer periphery of its open end 2. Annular sealing member 7 is provided on top of flange 3, and it is urgedly secured to open end 2a by first cap member 5. As a sealing member 7, and O-ring. Alternatively, sealing member 7 may be constituted by a lining rubber layer formed on the surface of first cap member 5 corresponding to open end 2.

First cap member 5 has first needle insertion through hole 6 formed in its center including axis X—X. Needle insertion through hole 6 is sealed with sealing member 4 as a sealing means with an anti-coagulation agent or the like sealed in the tube member and with a predetermined reduced pressure state maintained in the tube member. Sealing member 4 comprises gas barrier film member 4a, which is made from an aluminum foil, for instance, and is bonded to the outer end surface of cap member 5 to cover needle insertion through hole 6, and re-sealing member 4b made of natural rubber, for instance, and bonded to gas barrier film member 4a. The term "gas barrier" has the same meaning as described before in connection with the first embodiment. Re-sealing member 4b serves to re-seal a portion pierced by a needle (not shown) after blood collection.

The inner periphery of cap member 5 is formed with second thread 5a, which is a female thread. In correspondence to second thread 5a, the outer periphery of flange 3 of tube member 1 with a bottom is formed with first thread 3a, which is a male thread.

Cap member 5 is screwedly fitted on tube member 1 by turning its head. In this way, it can be readily and firmly secured to tube member 1 with sealingly member 7 interposed between it and open end 2 of tube member 1. This operation can be difficultly performed in a vacuum from the first step of fitting cap member 5 on open end 2a of tube member 1. Therefore, first cap member 5 is loosely fitted, and then in a vacuum it is tightened. By so doing, cap member 5 need be turned to a reduced extent in a vacuum, thus correspondingly facilitating the operation. Further, gas barrier film member 4a and re-sealing member 4b may be secured to cap member 5 either prior or subsequent to the fitting of cap member 5 on tube member 1.

When collecting blood with the blood collection tube assembled in the above way, a hollow needle provided in a needle holder (not shown) is forced to pierce re-sealing member 4b and gas barrier film member 4a and inserted through needle insertion through hole 6 of cap member 5 into tube member 1. Blood introduced from the tip of the needle flows through the hollow needle into the blood collection tube due to a reduced pressure state in tube member 1. In this way, blood collection is effected. When separating components of the collected blood, cap member 5 is removed by loosening it, whereby gas barrier film member 4a and re-sealing member 4b may be simultaneously removed. These components may be used again when sealing the tube again.

Thread structures 3a and 5a of flange 3 of tube member 1 and first cap member 5 are the same as in the previous embodiments.

FIG. 4 shows a fourth embodiment of the invention, with parts like those in the third embodiment designated by like reference numerals and symbols, a portion in the neighborhood of open end 2 of tube member 1 with a bottom being shown. In this embodiment, second cap member 8 with second needle insertion through hole 9 is fitted with strong friction on first cap member 5, thus urging sealing member 4 against first cap member 5. In this case, re-sealing member 4b of sealing member 4 need not be bonded to gas barrier film member 4b. However, the outer diameter of re-sealing member 4b is preferably made greater than the inner diameter of open end 2 as shown in FIG. 2 lest gas barrier film member 4a should sag downwardly by being urged by re-sealing member 4b when first cap member 5 is fitted on second cap member 8.

This arrangement permits accommodation of re-sealing member 4b is recess 10 formed in second cap member 8. Therefore, even if blood is attached to blood pool 4c provided on re-sealing member 4b after blood collection, blood pool 4c is not exposed at the upper end surface of second cap member 8, and thus the possibility of attachment of blood to hands is reduced. Further, in this embodiment the lower end of second cap member 8 is provided with annular hook 8a capable of snap engagement with lower end 5b of first cap member 5, as shown in FIG. 4. Thus, second cap member 8 can be more firmly fitted on first cap member 5. More specifically, once both cap members are fitted, hook 8a firmly engages with lower end 5b of first cap member 5 and thus the two cap members will not be readily detached.

In the third and fourth embodiments described above, sealing member 7 is ring-like in form. Alternatively, as in the first and second embodiment it is possible to use a disk-like sealing member having a sufficient thickness to provide a re-sealing property, thus dispensing with re-sealing member 4b. While the first to fourth embodiments have been described in the foregoing, they are by no means limitative can be variously modified without departing from the scope of the invention. For example, while aluminum foil is used for gas barrier film member 4a, it is possible it use a synthetic resin so long as to has a gas barrier, characteristic. Further, tube member 1 with a bottom may be made of glass instead of a plastic material. Further, while the above embodiments of the invention have been concerned with reduced pressure blood collection tubes for collecting blood, the invention is also applicable to other liquid collection tubes for collecting other body liquids or other liquids as well.

What is claimed is:

1. A liquid collection tube for collecting a liquid in its inside with a liquid collection needle, comprising:
   a bottomed cylindrical tube member having an open end and closed bottom at the other end thereof;
   a cap member removably mounted on said tube member at said open end thereof and having a needle insertion through hole therein corresponding in position to said open end of said tube member;
   sealing means coupled to said cap member to close said needle insertion through hole of said cap member, said sealing means being disposed in correspondence to said open end of said tube member and including:
   a gas barrier film element for maintaining said open end of said tube member hermetically sealed; and
   a re-sealing element secured to said gas barrier film element on the side thereof opposite said open end of said tube member;
   said sealing means being removable together with said cap member from said tube member; and
   a sealing member interposed between said cap member for said open end of said tube member for enhancing close sealing contact of said cap member with said open end of said tube member.

2. The liquid collection tube according to claim 14, wherein:
   said gas barrier film element of said sealing means is disposed in an overlapped relation to said sealing member; and
   said cap member urges an edge portion of said sealing member and said gas barrier film element overlapped over each other against an end surface of said open end of said tube member.

3. The liquid collection tube according to claim 2, wherein said re-sealing element is located in said through hole of said cap member.

4. The liquid collection tube according to claim 14, wherein said re-sealing element has an outer periphery fitted in a peripheral wall of said through hole of said cap member.

5. The liquid collection tube according to claim 14, wherein:
   said tube member has a first thread formed on an outer peripheral portion of said open end; and
   said cap member has a second thread formed on an inner peripheral portion thereof and which is meshed with said first thread.

6. The liquid collection tube according to claim 1 wherein:
   said gas barrier film element of said sealing means is disposed on an outer end surface of said cap member, said gas barrier film element having a peripheral wall which is in contact with said outer end surface of said cap member, and said through hole of said cap member is closed;
   the apparatus further comprising a second cap member for urging the outer periphery of said gas barrier film element against the outer end surface of said first-mentioned cap member, said second cap member having a needle insertion hole communicating with said through hole of said first-mentioned cap member via a sealing means and a hook engaging with said first-mentioned cap member to permit said first and second cap members to be removed together with said sealing means from said tube member.

7. The liquid collection tube according to claim 1, wherein said sealing means is provided on said cap member.

8. The liquid collection tube according to claim 1, wherein said sealing means is provided on the outside of said cap member.

9. The liquid collection tube according to claim 1, wherein said sealing means is provided under said cap member.

10. The liquid collection tube according to claim 9, wherein said sealing means is provided on a lower side of said cap member.

11. A liquid collection tube for collecting a liquid in its inside with a liquid collection needle, comprising:
    a bottomed cylindrical tube member having an open end and closed bottom at the other end thereof;
    a first cap member removably mounted on said tube member at said open end thereof and having a needle insertion through hole therein corresponding in position to said open end of said tube member;
    sealing means disposed in correspondence to said open end of said tube member and including a gas barrier film element for maintaining said open end of said tube member hermetically sealed;
    a sealing member interposed between said first cap member for said open end of said tube member for enhancing close sealing contact of said first cap member with said open end of said tube member;
    said gas barrier film element of said sealing means being disposed on an outer end surface of said cap member, said gas barrier film element having a peripheral wall which is in contact with said outer end surface of said first cap member and closing said through hole of said first cap member;
    a second cap member for urging the outer periphery of said gas barrier film element against the outer end surface of said first cap member, said second cap member having a needle insertion hole communicating with said through hole of said first cap member via a sealing means and a hook engaging with said first cap member to permit said first and second cap members to be removed together with said sealing means from said tube member.

12. The liquid collection tube according to claim 11, wherein:
    said sealing means further includes a re-sealing element mounted over said gas barrier film element toward the outside of said tube member; and
    said second cap member has a recess for accommodating said re-sealing therein element when said second cap member is fitted on said first cap member.

13. The liquid collection tube according to claim 12, wherein said recess of said second cap member has a wall surface urging said re-sealing element together with said gas barrier film element against said first cap member.

14. The liquid collection tube according to 11, wherein:

said tube member has a first thread formed on an outer peripheral portion of said open end; and said first cap member has a second thread formed on an inner peripheral portion thereof and which is meshed with said first thread.

15. The liquid collecton tube according to claim 11, wherein said sealing means is provided on said cap member.

16. The liquid collection tube according to claim 11, wherein said sealing means is provided on the outside of said cap member.

17. The liquid collection tube according to claim 11, wherein said sealing means is provided under said cap member.

18. The liquid collection tube according to claim 17, wherein said sealing means is provided on a lower side of said cap member.

19. A liquid collection tube for collecting a liquid in its inside with a liquid collection needle, comprising:

a bottomed cylindrical tube member having an open end and closed bottom at the other end thereof, said tube member having a first thread formed on an outer peripheral portion of said open end; and a cap member removably threadedly mounted on said tube member at said open end thereof and having a needle insertion through hole therein corresponding in position to said open end of said tube member, said cap member having a second thread formed on an inner peripheral portion thereof and which is meshed with said first thread;

sealing means coupled to said cap member to close said needle insertion through hole of said cap member, said sealing means being disposed in correspondence to said open end of said tube member and including:

a gas barrier film element for maintaining said open end of said tube member hermetically sealed; and said sealing means being removable together with said cap member from said tube member; and a sealing member interposed between said cap member for said open end of said tube member for enhancing close sealing contact of said cap member with said open end of said tube member.

20. The liquid collection tube according to claim 19, wherein said sealing means is provided on said cap member.

21. The liquid collection tube according to claim 19, wherein said sealing means is provided on the outside of said cap member.

22. The liquid collection tube according to claim 19, wherein said sealing means is provided under said cap member.

23. The liquid collection tube according to claim 22, wherein said sealing means is provided on a lower side of said cap member.

* * * * *

UNITED STATES PATENT AND TRADEMARK OFFICE
CERTIFICATE OF CORRECTION

PATENT NO. : 5,061,263
DATED : October 29, 1991
INVENTOR(S) : YAMAZAKI et al

It is certified that error appears in the above-identified patent and that said Letters Patent is hereby corrected as shown below:

Title page, Abstract:
    Line 2, delete "," after "needle".
    Line 4, adding a "," after the word "member" and deleting the "," after the word "tube".
Column 1, lines 9-10, change "character" to
    --characteristic--.
Column 5, line 36, before "top", insert --a--.
Column 5, line 40, change "and O-ring" to
    --an O-ring is used--.
Column 7, line 2, change "as to has" to --as it has--.
Column 7, line 35 (claim 2), change "claim 14" to --claim 1--.
Column 7, line 47 (claim 4), change "claim 14" to --claim 1--.
Column 7, line 51 (claim 5), change "claim 14" to --claim 1--.

Signed and Sealed this

Fourteenth Day of September, 1993

Attest:

BRUCE LEHMAN

*Attesting Officer*    *Commissioner of Patents and Trademarks*